United States Patent [19]

Mascellani et al.

[11] Patent Number: 4,668,784

[45] Date of Patent: May 26, 1987

[54] DERIVATIVES OF PYRIDO-BENZOTHIAZINE WITH HIGH ANTI-MICROBIAL ACTIVITY

[75] Inventors: Giuseppe Mascellani, Bologna; Arnaldo Fravolini, S. Sisto; Patrizia Terni, Milan, all of Italy

[73] Assignee: Mediolanum Farmaceutici S.R.L., Milan, Italy

[21] Appl. No.: 765,154

[22] Filed: Aug. 13, 1985

Related U.S. Application Data

[63] Continuation-in-part of Ser. No. 703,894, Feb. 21, 1985, abandoned.

[30] Foreign Application Priority Data

Feb. 24, 1984 [IT] Italy .............................. 19790 A/84

[51] Int. Cl.$^4$ ........................................... C07D 513/04
[52] U.S. Cl. ...................................................... 544/32
[58] Field of Search ........................... 544/32; 514/222

[56] References Cited

FOREIGN PATENT DOCUMENTS 57-203085 12/1982 Japan ..................................... 544/32

*Primary Examiner*—John M. Ford
*Attorney, Agent, or Firm*—Stevens, Davis, Miller & Mosher

[57] ABSTRACT

Pyrido-benzothiazine compounds having anti-microbial activity are prepared by (a) reacting 3-chloro-4-fluoroaniline with potassium thiocyanate and bromine to produce 2-amino-6-fluoro-7-chlorobenzothiazole, (b) reacting 2-amino-6-fluoro-7-chlorobenzothiazole with sodium hydroxide to produce the disulfide of 2-amino-5-fluoro 6-chlorothiophenol, (c) reacting the disulfide with sodium monochloroacetate to produce 7-fluoro-8-chloro-2H-1,4-benzothiazin-3(4H)-one, (d) reducing 7-fluoro-8-chloro-2H-1,4-benzothiazin-3(4H)-one to produce 7-fluoro-8-chloro-3,4-dihydro-2H-1,4-benzothiazone, (e) reacting 7-fluoro-8-chloro-3,4-dihydro-2H-1,4-benzothiazone with ethyl ethoxymethylenemalonate and cyclyzing the intermediate formed with polyphosphoric acid to produce ethyl 9-fluoro-10-chloro-7-oxo-2,3-dihydro-7H-pyrido[1,2,3 de] [1,4]-benzothiazine-6-carboxylate and (f) hydrolyizing the ethyl carboxylate to produce the corresponding carboxylic acid.

5 Claims, 3 Drawing Figures

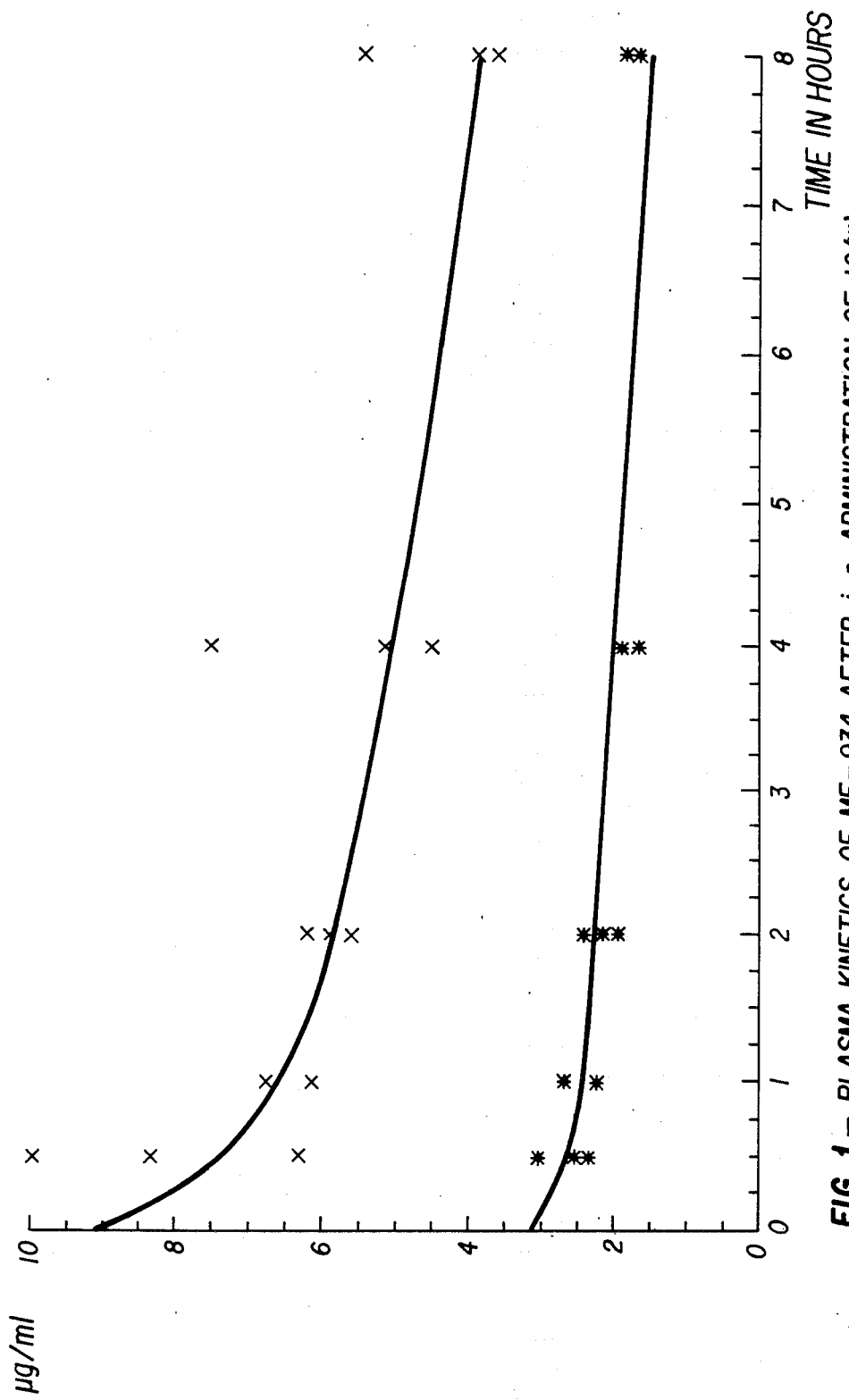
FIG. 1 — PLASMA KINETICS OF MF-934 AFTER i.p. ADMINISTRATION OF 10(*) AND OF 25(x) MG/KG TO RATS. MF-934 = COMPOUND (h)

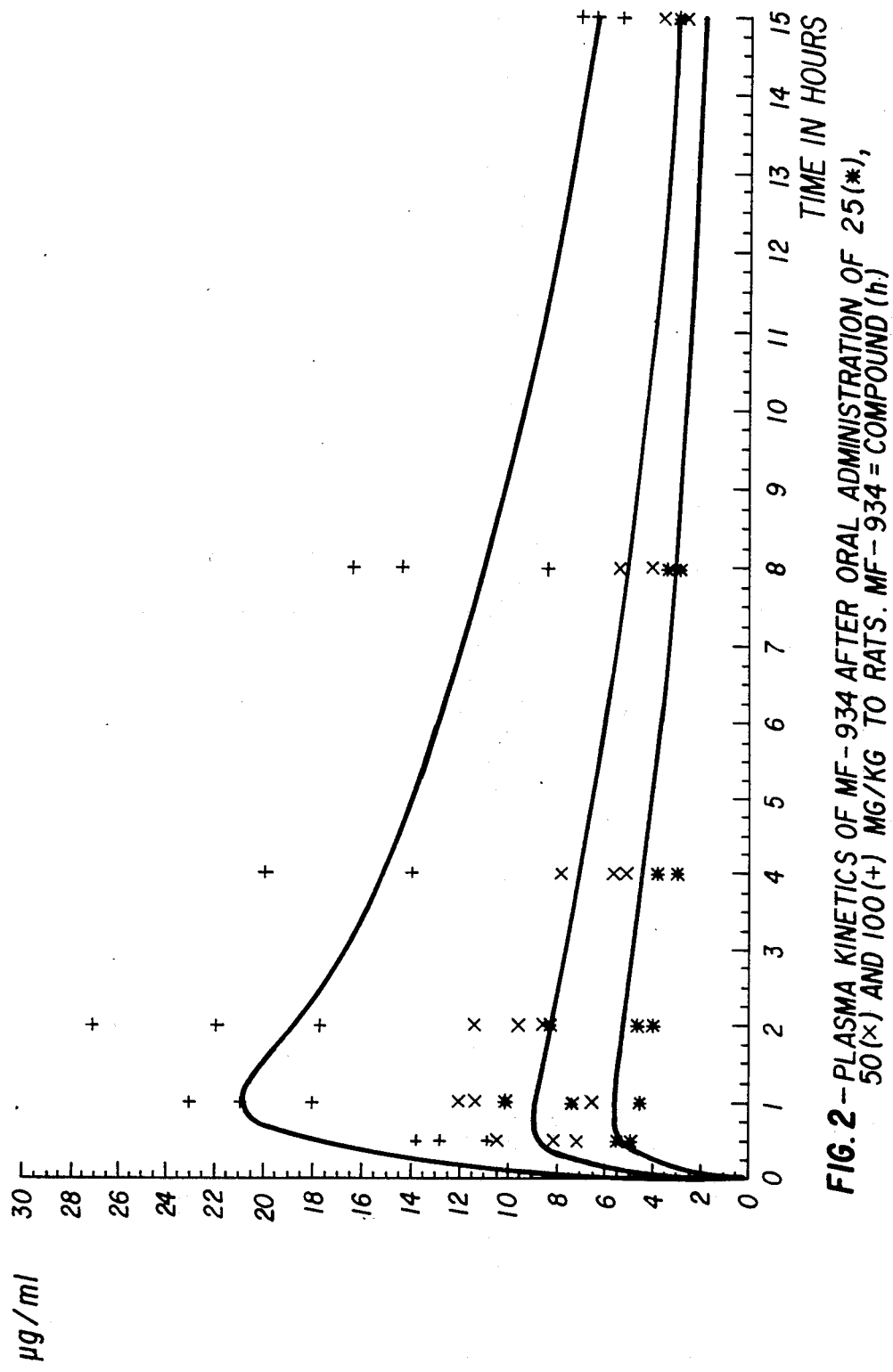
FIG. 2 – PLASMA KINETICS OF MF-934 AFTER ORAL ADMINISTRATION OF 25(∗), 50(×) AND 100(+) MG/KG TO RATS. MF-934 = COMPOUND (h).

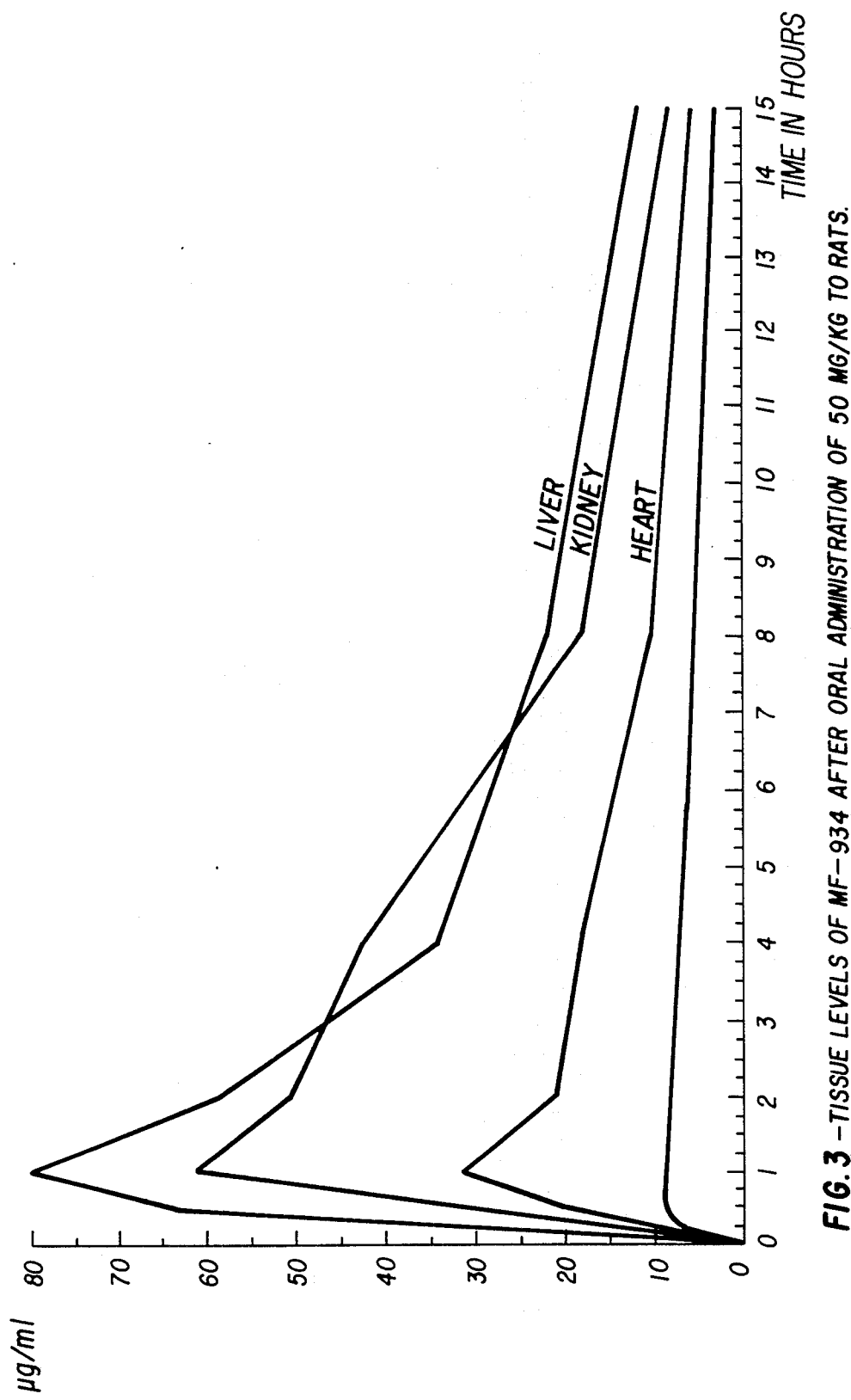

DERIVATIVES OF PYRIDO-BENZOTHIAZINE WITH HIGH ANTI-MICROBIAL ACTIVITY

This application is a continuation-in-part of our application Ser. No. 703,894, filed Feb. 21, 1985, and now abandoned.

The present invention relates to a new class of pyridobenzothiazine derivatives with high antimicrobial activity, and to the related processes for their preparation, as well as to the pharmaceutical compositions containing them.

Said pyrido-benzothiazine derivatives have the following general formula:

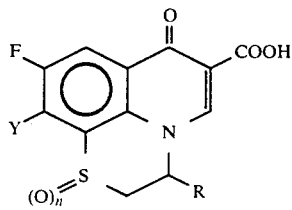

wherein R is H or $CH_3$; n is 0 or 1 or 2 and Y is Cl or F,

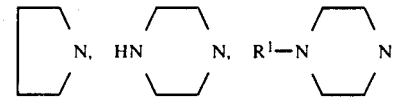

wherein $R^1$ is a $C_1$-$C_6$ alkyl, or a $C_2$-$C_6$ alkenyl or an arylalkyl, arylalkylcarbonyl, alkylcarbonyl, alkyloxycarbonyl, possibly substituted with halogens or hydroxy groups.

The derivatives of benzothiazine which are the object of the present invention constitute a class of antimicrobial agents effective also against the bacteria resistant to the classic antibiotics such as the penicillins, the streptomycin, and so on. They show moreover a notably higher antimicrobial activity comparatively to most presently known compounds; and are particularly useful in that they show antibacterial activity both against gram-positive and gram-negative bacteria, including Pseudomonas aeruginosa.

The compounds being the object of the present invention are synthesized starting from 7-fluoro-8-halogen-3,4-dihydro-2H-1,4-benzothiazine (II), wherein R is H or $CH_3$, which is obtained in its turn starting from 3-chloro-4-fluoroaniline or from 2,3,4-trifluoronitrobenzene, according to the series of reactions shown in schemes No. 1 and No. 2.

Scheme No. 1

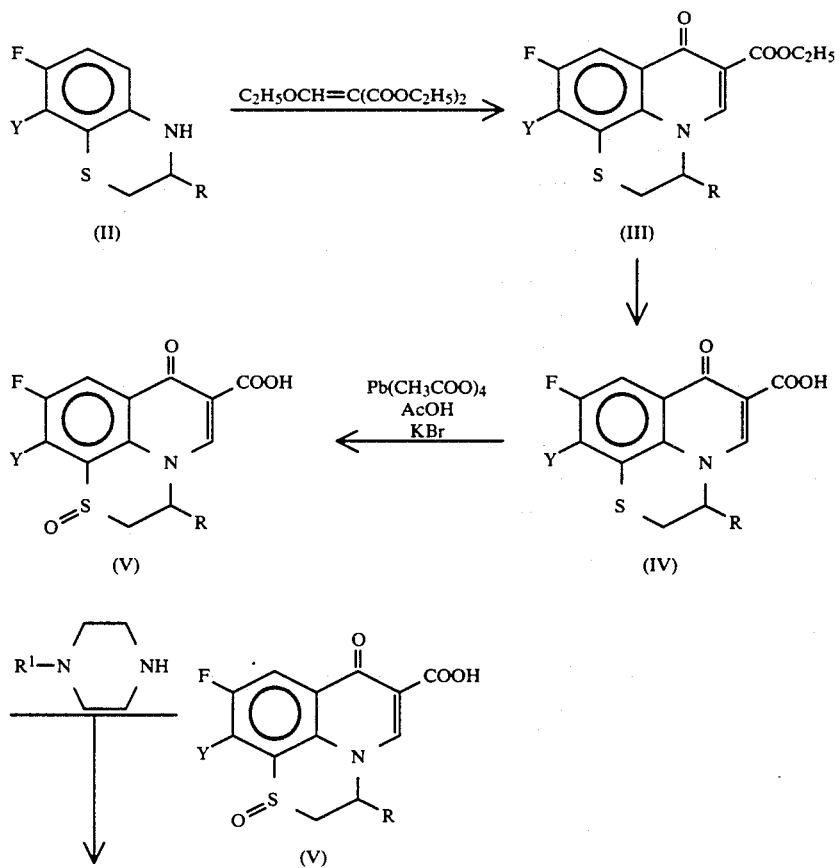

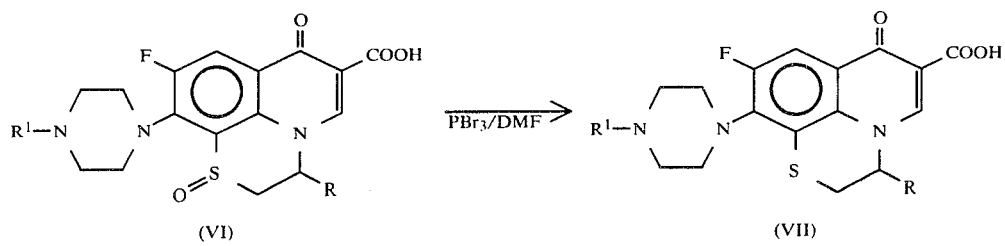

Wherein R, Y and $R^1$ have the meaning defined above.

The reaction of 7-fluoro-8-halogen-3,4-dihydro-2H-1,4-benzothiazine (II) with ethyl ethoxymethylenemalonate is preferably carried out within the temperature range of from 80° to 160° C., and may be carried out either in the presence or in the absence of solvent. The ring closure takes place in the presence of polyphosphoric acid.

The compound (III), ethyl 9-fluoro-10-halo-7-oxo-2,3-dihydro-7H-pyrido[1,2,3de][1,4]-benzothiazine-6-carboxylate, is hydrolyzed by means of sodium hydroxide into the corresponding acid (IV), which is oxidized to the sulphoxide in an acetic acid medium with a mild oxidizer such as lead tetraacetate at room temperature.

On the sulphoxide (V) the nucleophilic substitution is carried out by means of an amine of the type of possibly substituted piperazine, in an apolar aprotic organic solvent such as toluene or xylene, or in a polar aprotic organic solvent such as dimethyl sulphoxide or dimethylformamide or dimethylacetamide or sulpholane, at a temperature comprised within the range of from 70° to 160° C.

The reaction takes place within a time of from 1 to 24 hours. The substitution products (VI) are preferably reduced by means of phosphorus tribromide in dimethylformamide at room temperature to obtain products (VII). The intermediate compounds of formula (II) are obtained according to the reaction series of scheme No. 2.

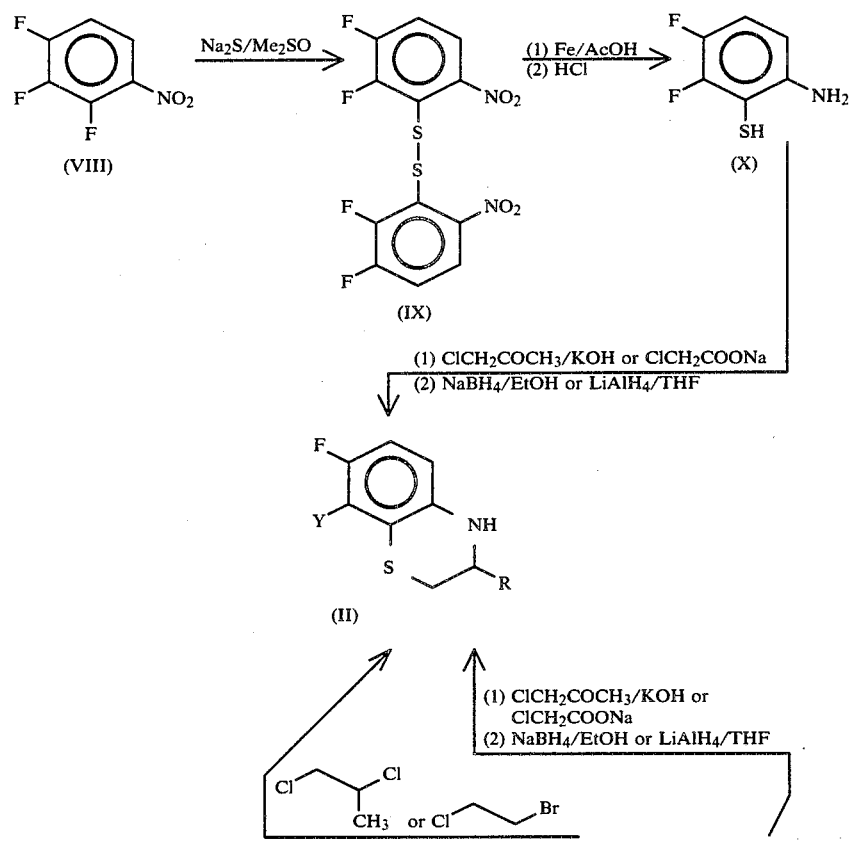

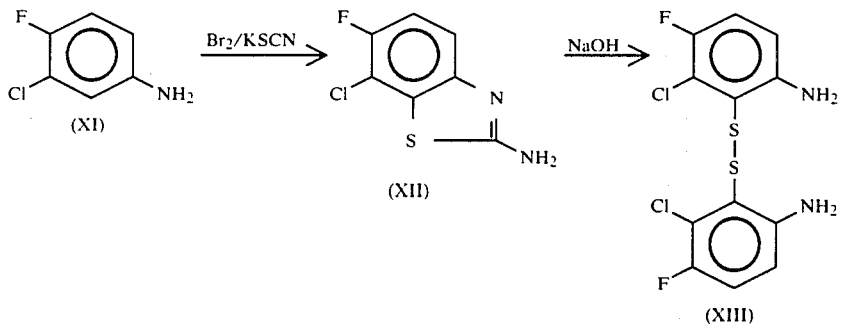

R = H, CH₃
Y = F, Cl

The disulphide (XIII), obtained by treating 6-fluoro-7-chloro-2-amino benzothiazole (XII) with NaOH, is treated with KOH in ethanol and to it monocloroacetone, or sodium monochloroacetate is added.

The mixture is made to react under refluxing conditions, the reaction mass is evaporated and the residue is extracted with chloroform.

The residue obtained by evaporating the chloroform is reduced with an excess of NaBH₄ in ethanol at 40°-60° C. over 1-2 hours.

When the compounds of formula (XIII) are reacted with sodium monochloroacetate, the corresponding substituted 2H-1,4-benzothiazine-3(4H) ones are obtained, which are reduced with LiAlH₄ in THF into compounds of formula (II) with R=H.

7-Fluoro-8-halogeno-3,4-dihydro-2H-1,4-benzothiazine (II) is thus obtained, wherein Y is Cl and R is H or CH₃. Always starting from the disulphide (XIII) the product (II) can be obtained by treatment with 1-bromo-2-chloroethane or with 1,2-dichloropropane.

Alternatively, the product (II) is obtained by the following process.

2,3,4-Trifluoronitrobenzene (VIII), obtained according to J.A.C.S. 81, 94 (1959), is heated in dimethyl sulphoxide at 85°-95° C. with sodium sulphide over 1-4 hours. The reaction mixture is cooled, the insoluble residue is filtered off and the filtrate is evaporated. The raw solid obtained is treated in acetic acid with iron dust. The reaction mixture is heated in water bath cautiously at the beginning, then under refluxing conditions over 1-2 hours, and is then filtered while still being warm. The filtrate is treated at high temperature with 37% hydrochloric acid and is kept at 75°-85° C. for 1-2 hours.

The mixture is diluted with water, is neutralized with sodium hydroxide and the solution is extracted with chloroform. The residue from chloroform evaporation is placed in ethanol, to it KOH and monochloroacetone is added, and the mixture is refluxed for 1-2 hours. The reaction mixture is evaporated and the residue is extracted with chloroform. The residue from chloroform evaporation is reduced with an excess of sodium borohydride in ethanol at 40°-60° C. for 1-2 hours, obtaining 7-fluoro-8-halogeno-3,4-dihydro-2H-1,4-benzothiazine (II), wherein Y is F and R is CH₃. When the reaction is carried out with sodium monochloroacetate, differently substituted 2H-1,4-benzothiazine-3(4H)one is obtained, which is reduced to the thiazine by means of LiAlH₄.

The compounds of the present invention can form salts by means of the addition of inorganic and organic acids such as hydrochloric, hydrobromic, methanesulphonic acid and the like; they can moreover form the corresponding carboxylates by means of the treatment thereof with sodium and potassium hydroxide. These compounds therefore may be administred both orally and by injection, as well as by means of external applications, by using the most suitable pharmaceutical forms.

The antibacterial activity (minimum inhibiting concentration, MIC) of the compounds according to the invention has been determined in agar, by adding the compound under evaluation at concentrations of from 0.1 to 10o mcg/ml by means of a "multipoint inoculator" (Denley Techn. Ltd., England); the medium used was Isosensitest agar (Oxoid); the bacterial inoculate was $10^4$ colony forming unity (CFU) per inoculation point. The reading of the results was done after 24 hour-incubation in thermostat at 37° C.

The MIC was defined as the lowest concentration of chemotherapeutic agent still capable of totally inhibiting the growth of bacteria, as detected from a lack of colony development in the inoculation point.

The microorganisms used for evaluating the activity of the specific compounds have been: Escherichia coli, Klebsiella P., Enterobacter, Serratia, Citrobacter, Proteus (+), Salmonella, Pseudomonas, Staphylococcus.

All the compounds according to the present invention are provided with antibacterial activity against one or more microorganism(s) among those above mentioned. Some of such compounds are absorbed after having been administered orally to the animals, and are particularly useful as disinfectants of the urinary tract in that they are excreted in a high percentage (50-70% over 24 hours after the administration of 50 mg/kg per os) as such, and in metabolic active form, through the urine.

Other compounds according to the present invention are absorbed only to a very small extent (1% of urinary excretion over 24 hours after the administration of 50 mg/kg per os), and can therefore be particularly useful as disinfectants of the intestinal tract.

The acute toxicity of the compounds according to the present invention is generally low. In particular, the therapeutical index $ED_{50}/LD_{50}$, considering the high extent of oral absorption of some of them, is extremely favourable.

The results of the tests of antibacterial activity of the products according to the invention, and of some comparison products, are reported in following Table 1.

TABLE 1

Activity expressed as MIC (mcg/ml) for compounds of formula

| Compound | R | X | Y | n | A | B | C | D | E | F | G |
|---|---|---|---|---|---|---|---|---|---|---|---|
| (a) | H | F | Cl | 0 | 0.39 | >25 | 0.39 | 1.56 | 0.78 | 0.39 | 0.78 |
| Comparison (b) | H | Cl | Cl | 0 | >50 | >50 | 0.78 | 6.25 | 12.5 | >50 | >50 |
| (c) | H | F | ⟨N⟩ (pyrrolidinyl) | 0 | 1.56 | 3.12 | <0.39 | 3.12 | 1.56 | 1.56 | 25 |
| Comparison (d) | H | Cl | ⟨N⟩ (pyrrolidinyl) | 0 | >50 | >50 | 0.78 | 3.12 | 12.5 | >50 | >50 |
| (e) | H | F | ⟨N⟩ (pyrrolidinyl) | 1 | 12,5 | >50 | 12,5 | >50 | 25 | 50 | 50 |
| (f) | H | F | ⟨N⟩ (pyrrolidinyl) | 2 | 3.12 | >50 | 3.12 | >50 | 25 | 25 | 25 |
| (g) | H | F | HN⟨piperazinyl⟩N | 0 | 0.39 | 12.5 | 0.78 | 1.56 | <0.39 | <0.39 | 0.78 |
| (h) | H | F | CH₃N⟨piperazinyl⟩N | 0 | 0.78 | >50 | 0.78 | 1.56 | <0.39 | <0.39 | 1.56 |
| (i) | H | F | CF₃CH₂N⟨piperazinyl⟩N | 0 | >50 | >50 | 0.39 | >50 | >50 | >50 | 12.5 |
| (l) | H | F | CF₃CO—N⟨piperazinyl⟩N | 0 | <0.39 | 12.5 | 1.56 | 1.56 | <0.39 | <0.39 | 0.39 |
| (m) | H | F | 2,6-dimethylpiperazinyl (CH₃, HN, N, CH₃) | 0 | 6.25 | 100 | 3.12 | 25 | 6.25 | 3.12 | 12.5 |
| (n) | CH₃ | F | Cl | 0 | 0.39 | 25 | 0.39 | n.d. | 0.78 | 0.39 | n.d. |
| (o) | CH₃ | F | F | 0 | 0.39 | 12.5 | 0.39 | n.d. | 0.78 | 0.39 | n.d, |

TABLE 1-continued

Activity expressed as MIC (mcg/ml) for compounds of formula

[structure diagram showing quinolone with X, Y substituents, COOH group, N with CH2-CHR-O(=O)n side chain]

| Compound | R | X | Y | n | Bacterial stocks (*) |  |  |  |  |  |  |
|---|---|---|---|---|---|---|---|---|---|---|---|
|   |   |   |   |   | A | B | C | D | E | F | G |
| (p) | CH$_3$ | F | CH$_3$N⟨⟩N | 0 | 0.78 | 50 | 0.78 | n.d. | <0.39 | <0.39 | n.d. |
| Comparison (q) | CH$_3$ | Cl | CH$_3$N⟨⟩N | 0 | >50 | >12.5 | 3.12 | n.d. | 12.5 | >50 | n.d. |
| (r) | CH$_3$ | F | HN⟨⟩N | 0 | 0.78 | 12.5 | 0.78 | n.d. | <0.39 | <0.39 | n.d. |

(*) Bacterial stocks:
A = *Escherichia coli* (981)
B = *Pseudomonas aeruginosa*
C = *Staphylococcus aureus*
D = *Proteus Morgani* (indole +)
E = *Klebsiella pneumoniae*
F = *Enterobacter*
G = *Citrobacter*

The results reported in Table 1 demonstrate the considerable antibacterial activity of the pyrido-benzothiazine derivatives according to the invention. In particular, by comparing the activity displayed by the compounds (a), (c) and (p) with the activity displayed by the compounds (b), (d) and (q), it is noticed how critical is the presence of fluorine in the X-position: when indeed in the X-position chlorine is present instead of fluorine, the activity of the compound is strongly reduced.

Moreover we have found that although some of the new pyrido-benzothiazine according to the invention, and namely the compounds indicated with (a), (c), (g), (h), (l), (n), (o), (p), (r) in Table 1, show a very good and comparable anti-bacterial activity "in vitro", only one of them, i.e. the compound (h), shows when tested in vivo characteristics accounting in the whole for a systemic antibacterial compound having long-lasting activity. Such a kind of activity is actually surprising since none of the quinolones presently on the market has a long-lasting activity; they all are exclusively used as disinfectant of the urinary tract.

We give hereinafter in Table 2 the haematic levels of compound (h) as measured in plasma by HPLC. Each value is the average of three tested rats.

TABLE 2

Plasma levels (μg/ml M ± S.D.) after intraperitoneal and oral administration to rats of compound (h).

| Dose mg/kg | route of administration | Time elapsed after administration in hours |  |  |  |  |  |
|---|---|---|---|---|---|---|---|
|   |   | 0.50 | 1 | 2 | 4 | 8 | 15 |
| 10 | i.p. | 2.70 ± 0.36 | 2.53 ± 0.29 | 2.17 ± 0.15 | 1.83 ± 0.11 | 1.63 ± 0.06 | n.t. |
| 25 | i.p. | 8.35 ± 1.00 | 6.29 ± 0.45 | 6.44 ± 0.97 | 5.01 ± 0.46 | 3.72 ± 0.13 | n.t. |
| 25 | os. | 5.33 ± 0.29 | 7.30 ± 2.80 | 5.67 ± 2.47 | 3.60 ± 0.52 | 3.27 ± 0.23 | 2.73 ± 0.11 |
| 50 | os. | 8.75 ± 1.75 | 10.06 ± 2.95 | 9.95 ± 1.41 | 6.37 ± 1.41 | 4.95 ± 0.78 | 4.29 ± 0.53 |
| 100 | os. | 12.47 ± 1.46 | 20.58 ± 2.53 | 22.19 ± 4.65 | 15.92 ± 3.44 | 13.01 ± 4.17 | 6.22 ± 0.88 | n.t. = not tested

In the FIGS. 1 and 2 the plasma kinetics of the compound (h) are also graphically reported.

More precisely in FIG. 1 the plasma levels in rats versus the time, are reported, after i.p. administration of 10 mg/kg and 25 mg/kg of compound (h), while in FIG. 2 the plasma levels are reported of compound (h) in rats, versus the time, after oral administration of 25, 50 and 100 mg/kg of said compound.

The data of Table 2 and of FIGS. 1 and 2 demonstrate that the compound (h) is quickly absorbed either per os and i.p., in a dose-depending amount, and that it induces high and long-lasting plasma levels. An half-life time of 10 hours may be deduced from the reported values. Nothing like this has been found with the remaining compounds of Table 1 with which a maximum half-life value of 4 hours has been determined.

What above accounts for the fact that the compound (h) is the only long-acting, strong antibacterial compound in the new class.

In Table 3 the tissue levels of compound (h), at various times after oral administration, are reported.

The amounts of compound (h) have been measured by HPLC and each value is the average of three tested rats.

TABLE 3

| Tissue | Tissue levels (μg/ml) M ± S.D.) after oral administration to rats of 50 mg/kg of compound (h) | | | | | |
|---|---|---|---|---|---|---|
| | Time elapsed after administration, in hours | | | | | |
| | 0.5 | 1 | 2 | 4 | 8 | 15 |
| heart | 19.98 ± 9.57 | 31.36 ± 8.15 | 21.03 ± 8.07 | 18.06 ± 2.00 | 9.93 ± 1.40 | 5.35 ± 1.45 |
| kidney | 32.64 ± 2.33 | 61.20 ± 31.58 | 50.56 ± 28.63 | 42.35 ± 2.40 | 17.83 ± 3.69 | 7.95 ± 2.03 |
| liver | 63.52 ± 21.49 | 80.42 ± 36.79 | 58.12 ± 23.09 | 34.08 ± 5.82 | 21.59 ± 1.87 | 11.31 ± 2.46 |
| plasma | 8.75 ± 1.75 | 10.06 ± 2.96 | 9.95 ± 1.41 | 6.37 ± 1.41 | 4.95 ± 0.78 | 4.29 ± 0.53 |

For a ready comparison, the values of Table 3 are graphically reported in FIG. 3, together with the plasma levels deduced from Table 2. It is thus immediately evident that the compound (h) reaches mean tissue levels, at the moment of peak, of 10.1 μg/ml in plasma, 31.4 μg/ml in heart, 61.2 μg/ml in liver, 80.4 μg/ml in liver, i.e. the compound (h) shows a very high capacity of distribution and concentration in the various organs, with a ratio constatly higher than 3 with respect to the concentration in plasma.

No presence of the compound (h) has been detected in brain. No other compound among those of Table 1 has shown a so wide-spread distribution in the various organs and at so high levels.

As precedently said, the data demonstrate that the compound (h), at difference of the remaining compounds of the same class and of the antibacterial quinolones known up today, may act as a highly effective systemic antibacterial compound.

In Table 4 the percentage of urinary excretion of compound (h) is reported, as measured in the 24 hours successive to oral administration of the same to rats.

Each value is the average of three tested rats.

The tests have been performed in comparison with Ofloxacin, a well known antibacterial compound. The amount of excreted product has been determined with microbiological analysis, by using Klebsiella Pneumoniae as the testing microorganism.

TABLE 4

| Percent urinary excretion in the 24 hours successive to oral administration to rats of compound (h) | | |
|---|---|---|
| Product | mg/kg per os | Percent urinary excretion M ± S.D. |
| Compound (h) | 20 | 77.33 ± 6.81 |
| Compound (h) | 50 | 73.00 ± 4.58 |
| Ofloxacin | 20 | 61.00 ± 4.58 |
| Ofloxacin | 50 | 54.50 ± 5.29 |

Since the amount of compound (h) in the urine has been microbiologically evaluated, the test of Table 4 means that the compound according to the invention, after having reached all the main organs, is excreted in an amount as high as 75% still in the active form, without having undergone metabolic degradation.

Particularly interesting is the comparison with Ofloxacin showing that the amount of still active compound (h) is 1.3 times higher than that of Ofloxacin under the same testing conditions.

The remaining compounds of Table 1 have given in the same test an average urinary excretion of still active compound over the 24 hours of 12%.

Preliminary tests performed in dogs with the compound (h) have given still better results than the tests performed in rats. For example by administering to dogs 20 mg/kg per os of compound (h) sharply higher plasma levels than with the same amounts in rats are reached, with a peak at 8 μg/ml. Also the half-life in dogs (24 hours) is well higher than in rats (10 hours).

By summing up the tests of pharmacocynetica performed with the compounds of Table 1, have shown that only the compound (h) possesses the property of reaching high and long-lasting levels both in the plasma and in the various organs, besides a very high half-life, all this accounting in the whole for a long-acting antibacterial compound to be used in systemic infections.

Such an use would be quite distinct from that common for structurally analogous antibacterial products presently on the market, only used as disinfectants of urinary tract.

Moreover the compound (h) may form water soluble salts with organic or inorganic pharmaceutically acceptable acids (such as hydrochloric, hydrobromic, methansulphonic, oxalic, succinic acid and so on) or with bases such as sodium or potassium hydroxides, thus allowing the possibility of intraperitoneal injection, particularly important for antibacterial treatment of patients having upset gastric functionality. None of the antibacterial quinolones presently on the market may be i.p. injected.

Among the compounds of Table 1 also the compound (a) has surprisingly given, when pharmacocynetically tested, results quite different from those of the remaining compounds. Namely it has been found that the compound (a) is not all absorbed, thus suggesting its use as topical disinfectant or as selective antibacterial drug for the gastroenteric tract.

Both the compounds (h) and the compound (a) may be formulated with the usual pharmaceutical diluents, solvents and supports.

The following Examples are reported to the purpose of illustrating, not limiting, the process for the preparation of the pyrido-benzothiazine derivatives according to the present invention.

EXAMPLE 1

Preparation of compound of general formula (I) with R=H, Y=Cl and n=0

For the preparation of the compound of general formula (I) with R=H; Y=Cl and n=0, as starting product 3-chloro-4-fluoroaniline (XI) is used, which is reacted with potassium thiocyanate and bromine as follows.

Into a flask kept under mechanical stirring, 20 ml of acetic acid, 8 g of the aniline (XI) and 10.7 g of KSCN, dissolved in 100 ml of acetic acid, are added.

To this mixture, 9.2 g of $Br_2$ dissolved in 19 ml of acetic acid are added, taking care that the temperature does not increase over 30°-35° C., and the mixture in kept under these conditions for one hour.

The insoluble solid (a) is filtered. The filtrate is made alkaline with concentrated $NH_3$ and the precipitate formed is collected by filtration (b).

The solid (a) is washed twice with water, keeping it stirred for 30 minutes. The insoluble portion obtained is constituted by isomer of compound (XII) with Cl in the 5-position. The solid (b) is washed with water. It is constituted by the compound (XII) and by its isomer with chlorine in the 5-position, in a 50:50 ratio to each other. Overall yield: 87%.

The separation, with 1/1 benzene/AcOEt on a silica gel column, yields the pure products having the following characteristics:

2-amino-5-chloro-6-fluoro benzothiazole: m.p. 217°-220° C.

IR (nujol) 3,465 cm$^{-1}$, 3,285 cm$^{-1}$(NH)

$^1$H-NMR (DMSO-TMS) δppm 7.55 (1H, d, $C_4$—$\underline{H}$, $J_{H-F}$≃7.5 Hz), 7.92 (1H, d, $C_7$—$\underline{H}$), $J_{H-F}$≃9).

2-amino-6-fluoro-7-chloro benzothiazole (XII): m.p. 189°-192° C.

2-amino-6-fluoro-7-chloro benzothiazole (XII): m.p. 189°-192° C.

I.R. (nujol) 3,390 cm$^{-1}$, 3,250 cm$^{-1}$ (N—H)

$^1$H-NMR (DMSO-TMS) δppm 7.2 (2H, m, aromatic) 7.7 (2H, s, —$NH_2$).

The product (XII) is reacted with NaOH as follows.

The product (XII) is suspended in NaOH solution at 50% concentration and is refluxed allowing formed $NH_3$ to escape; the reaction is allowed to proceed for 24 hours. The mixture is diluted with $H_2O$ while being still warm, and is then made acid to pH 5 by means of acetic acid. A precipitate is formed, which is filtered off. The solid is washed with chloroform. The filtrate is extracted with chloroform.

The chloroform phases are combined, dried on sodium sulphate and evaporated in vacuo to yield a solid residue. The disulphide (XIII), a yellow solid, is obtained, with a yield of 62%.

The product (XIII) is reacted with sodium monochloroacetate as follows.

To an amount of 4 g of the product (XIII) dissolved in 10 ml of ethyl alcohol a solution of 1.2 g of NaOH in 10 ml of water is added. The mixture is heated at 40°-50° C. until the solid is completely dissolved, and then a solution formed by 2.57 g of chloroacetic acid and 1 g of NaOH in 6 ml of $H_2O$ is added dropwise.

The reaction is allowed to proceed at boiling temperature for 50 minutes, the mixture is poured into icy water and is made acid with 6N HCl.

The product formed is filtered, washed with $H_2O$ and oven dried.

The product constituted by 7-fluoro-8-chloro-2H-1,4-benzothiazin-3(4H)-one is thus obtained, with an overall yield of 83%.

This product is reacted with $LiAlH_4$ as follows. In a flask of 250 ml provided with mechanical stirrer 1.06 g of $LiAlH_4$ are suspended in 20 ml of tetrahydrofuran, and the suspension is refluxed. A solution constituted by 3.8 g of the product in 80 ml of tetrahydrofuran is dropwise, very slowly, added.

When the addition is ended, the reaction mixture is made boil for 30 minutes, then it is cooled, and the excess of $LiAlH_4$ is destroyed with HCl at 10% concentration, the mixture is filtered and the filtrate is made alkaline by means of 1N NaOH. Tetrahydrofuran is evaporated under vacuum and the residue is extracted with chloroform. The chloroform phase is thoroughly dried and evaporated, and the product (II) with R=H and Y=Cl is obtained, with a yield of 80% and with the following characteristics:

$^1$H-NMR (DMSO-TMS) δppm 3.1 (2H, m, —$CH_2$—N), 3.55 (2H, m, $CH_2$—S), 6.17 (1H, N—H), 6.70 (2H, m, aromatic residues).

The product (II) is reacted with ethyl ethoxymethylenemalonate as follows.

An amount of 1.58 g of product (II) is reacted with 1.9 ml of ethyl ethoxymethylenemalonate at 120° C. under stirring for 1 hour and 45 minutes; 5.5 g of polyphosphoric acid are then added, keeping the temperature at the value of 160° C. for one hour.

At the end of this time, the reaction mass is cooled and treated with icy water. The dark-coloured dense oil obtained is broken up by stirring. The thus formed solid is filtered off and washed with water.

An amount of 2.33 g of ethyl 9-fluoro-10-chloro-7-oxo-2,3-dihydro-7H-pyrido[1,2,3de][1,4]benzothiazine-6-carboxylate [compound (III) with R=H and Y=Cl] is obtained. Yield 92%.

$^1$H NMR ($CF_3COOH$—TMS) δppm 1.6 (3H, t, $OCH_2$—$CH_3$), 3.62 (2H, m, —$CH_2$—N), 4.72 (2H, q, O—$CH_2$), 5.13 (2H, m, S—$CH_2$), 8.15 (1H, d, $C_8$—$\underline{H}$, $J_{H-F}$≃7.5 Hz), 9.3 (1H, s, $C_5$—$\underline{H}$).

The compound (III) is reacted with NaOH: an amount of 1 g of product (III) is reacted with 45 ml of NaOH at 10% concentration under refluxing conditions for one hour. The mixture is cooled, poured into icy water and then made acid with HCl, filtered and then washed with $H_2O$.

An amount of 0.68 g of 9-fluoro-10-chloro-7-oxo-2,3-dihydro-7H-pyrido[1,2,3de][1,4]benzothiazine-6-carboxylic acid [compound (I) with R=H; Y=Cl and n=0] is obtained with a yield of 75%.

The product has the following characteristics:

$^1$H-NMR ($CF_3COOH$, TMS) δ ppm 3.68 (2H, m, N—$CH_2$) 5.28 (2H, m, S—$CH_2$), 8.22 (1H, d, $C_8$—$\underline{H}$, $J_{H-F}$-8); 9.40 (1H, s, $C_5$—$\underline{H}$).

IR (nujol) 3,070 cm$^{-1}$ (C—H), 1,718 cm$^{-1}$ (C=O).

UV (EtOH) $\lambda_{max}$ 253, 341 mμ; m.p. 311°-313° C.

EXAMPLE 2

Preparation of the compound of general formula (I) wherein R=H; Y=Cl and n=2

The preparation of the compound of general formula (I) with R=H, Y=Cl and n=2 is carried out by treating with $H_2O_2$ the compound (I) with R=H; Y=Cl and n=0 obtained from Example 1.

An amount of 1.5 g of said compound (I) is suspended in 150 ml of acetic acid, the suspension is heated to 100°

C. and to it 6 ml of 30% —H$_2$O$_2$ dissolved in 30 ml of acetic acid are added.

The reaction is allowed to proceed at 110° C. for 3 hours, the reaction mass is then cooled. The precipitated solid is filtered off and washed with H$_2$O: an amount of 1.1 g is obtained of product: 9-fluoro-10-chloro-7-oxo-2,3-dihydro-7-H-pyrido-[1,2,3de][1,4]benzothiazine-1,1-dioxide-6-carboxylic acid, i.e. of the sulphone of formula:

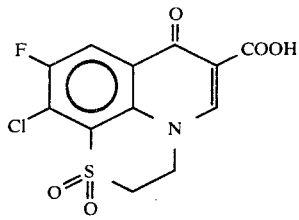

By drying up the washing liquors, a further 0.17 g of product is obtained, with an overall yield of 76,5%.

M.p. 321°-323° C.

IR (nujol) 3,075 cm$^{-1}$, 1,128 cm$^{-1}$, 1,149 cm$^{-1}$, 1,170 cm$^{-1}$.

UV (EtOH) λ$_{max}$ 221, 269, 352 mμ.

| Elemental analysis: | | | |
|---|---|---|---|
| Found % | C = 43.72 | H = 2.12 | N = 4.31 |
| Theoretical % | C = 43.45 | H = 2.12 | N = 4.22 |

EXAMPLE 3

Preparation of the compound of general formula (I) wherein R=H;

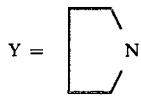

and n=2

The preparation of the compound of general formula (I) with R=H;

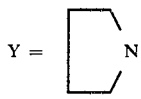

and n=2 is carried out by reacting with pyrrolidine the sulphone obtained in Example 2. An amount of 0.7 g of the sulphone is suspended in 7 ml of toluene, 1.75 ml of pyrrolidine are added and the reaction is carried out at boiling temperature over 2.5 hours. The reaction mixture is cooled and filtered: the solid is constructed by 0.6 g of the pyrrolidine salt of 9-fluoro-10-(1-pyrrolidinyl)-7-oxo-2,3-dihydro-7H-pyrido[1,2,3 de][1,4]benzothiazine-1,1-dioxido-6-carboxylic acid, with a yield of 65%.

M.p. 285°-289° C.

$^1$H-NMR (CF$_3$COOH-TMS) δppm 2.28 (8H, m, —CH$_2$—CH$_2$—), 3.6 (4H, m), 4.32 (4H, pyrrolidine), 4.08 (2H, m, N—CH$_2$), 5.46 (2H, m, S—CH$_2$), 8.35 (1H, d, C$_8$—H, J$_{H-F}$=13.5 Hz), 9.23 (1H, s, C$_5$—H).

IR (nujol) 1,630 cm$^{-1}$, 1,605 cm$^{-1}$, 1,199 cm$^{-1}$, 1,167 cm$^{-1}$, 1,125 cm$^{-1}$, 1,075 cm$^{-1}$.

UV (EtOH) λ$_{max}$ 214, 246, 264, 282, 359 mμ.

EXAMPLE 4

Preparation of the compound of general formula (I) wherein R=H; Y=Cl and n=1

The preparation of the compound of general formula (I) wherein R=H, Y=Cl and n=1 is carried out by reacting the compound (I) with R=H; Y=Cl and n=0 with lead tetraacetate. An amount of 3 g of said compound (I) is suspended in a solution constituted by 300 ml of H$_2$O and 1,000 ml of acetic acid, 70 mg of KBr are added, and, while following the course of the reaction by means of a potentiometer equipped with Pt-calomel electrodes, 170 ml of a 0.065M solution of Pb(OAc)$_4$ in acetic acid are slowly added at the temperature of 30° C. The potential increases slowly from the value of 475 mV measured before starting the addition of Pb(OAc)$_4$ to the value of 1,040 mV measured after the addition of 170 ml of Pb(OAc)$_4$.

When the addition of Pb(OAc)$_4$ is ended, the solvent is evaporated and the product is crystallized from acetic acid, thus 1.7 g of the sulphoxide of formula

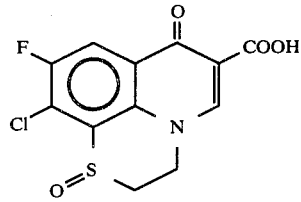

being obtained, with a yield of 54%.

M.p. 294°-298° C.

$^1$H-NMR (CF$_3$COOH-TMS) δppm 8.74 (1H, d, C$_8$—H, J$_{H-F}$=7 Hz) 9.7 (1H, s, C$_5$—H).

IR (nujol) 1,049 cm$^{-1}$, 1,029 cm$^{-1}$.

UV (EtOH) λ$_{max}$ 224, 270, 354 mμ.

| Elemental analysis | | | |
|---|---|---|---|
| Theoretical % | C = 45.65 | H = 2.23 | N = 4.43 |
| Found % | C = 45.24 | H = 2.20 | N = 4.21 |

T.L.C. in MeOH: Sulphone-related R$_f$=0.78.

EXAMPLE 5

Preparation of compounds of general formula (I) wherein R=H;

with n respectively equal to 1 or equal to 0

The preparation of the compound of general formula (I) wherein R=H;

Y = 

and n=1 has been carried out by means of the reaction with pyrrolidine of the sulphoxide obtained at Example 4.

An amount of 0.66 g of sulphoxide is suspended in 70 ml of toluene, 1.7 ml of pyrrolidine are added and the reaction is allowed to proceed for 2.5 hours under refluxing conditions. At the end of the reaction, the reaction mass is filtered and 0.48 g of solid product are recovered with a yield of 65%. The product is constituted by 9-fluoro-10(1-pyrrolidinyl)7-oxo-2,3-dihydro 7H-pyrido[1,2,3 de][1,4]benzothiazine-1-oxido-6-carboxylic acid having the following characteristics:

M.p.=253°–255° C.

$^1$H-NMR (CF$_3$COOH—TMS) δppm 8.19 (1H, d, C$_8$—H, J$_{H\text{-}F}$≃14.25 Hz), 9.32 (1H, s, C$_5$—H).

IR (nujol) 3,035 cm$^{-1}$, 1,758 cm$^{-1}$, 1,610 cm$^{-1}$, 1035 cm$^{-1}$.

UV (EtOH) λ$_{max}$ 294, 346 mμ.

| Elemental analysis | | | |
|---|---|---|---|
| Theoretical % | C = 54.85 | H = 4.31 | N = 7.99 |
| Found % | C = 54.36 | H = 4.33 | N = 7.81 |

By reducing the sulphoxide group of the product obtained, the compound of general formula (I) with R=H;

Y = 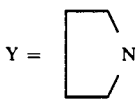

and n=0 is obtained.

The reduction is carried out by means of the following process.

An amount of 0.5 g of the sulphoxide obtained as described above is dissolved at room temperature in 90 ml of dimethylformamide. The reaction mass is cooled to 0° C. and of phosphorus tribromide are added. It is allowed to react at this temperature for 20 minutes and then 40 ml of water are added. It is stirred for 1 hour and the precipitate thus formed is filtered, wasted with water and dried.

An amount of 0.35 g of 9-fluoro-10(1-pyrrolidinyl)-7-oxo-2,3-dihydro-7H-pyrido[1,2,3de][1,4]benzothiazine-6-carboxylic acid is obtained with a yield of 72%. The product shows the following characteristics: M.p. 290°–292° C.

| Elemental analysis: | | | |
|---|---|---|---|
| Theoretical % | C = 57.48 | H = 4.52 | N = 8.37 |
| Found % | C = 57.23 | H = 4.68 | N = 8.35 |

$^1$H-NMR (CH$_3$COOH—TMS) δppm 8.35 (1H, d, C$_8$—H), J$_{H\text{-}F}$≃9.52 Hz), 9.5 (1H, s, C$_5$—H).

IR (nujol): the

group frequency (1,048 cm$^{-1}$) disappears.

EXAMPLE 6

Preparation of the compounds of general formula (I) wherein R=H;

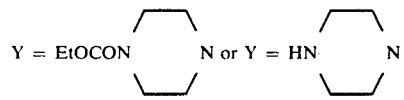

and with n=1 or n=0

9-Fluoro-10-[N-(4'-ethoxycarbonyl)-piperazinyl]-7-oxo-2,3-dihydro-7H-pyrido[1,2,3de][1,4]benzothiazine-1-oxido-6-carboxylic acid An amount of 0.5 g of the sulphoxide:

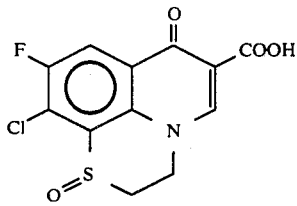

is suspended in 20 ml of dimethyl sulphoxide. To it 1.75 g of N-ethoxycarbonyl-piperazine are added and the mixture is heated. When the temperature of the reaction mass is of about 100° C., the complete dissolving of the product takes place. The temperature is increased to 140° C. and is maintained at this value for 1 hour, a precipitate being thus formed. The precipitate is filtered off and the filtrate is evaporated. The residue is treated with ethanol and diethyl ether, a second precipitate being obtained, which is combined with the first one.

A total amount of 0.5 g of the compound (I) with R=H;

Y = EtOCON 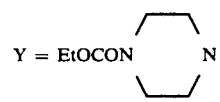

and n=1 is obtained, with a yield of 75%.

$^1$H-NMR (CF$_3$COOH—TMS) δppm 1,41 (3H, t, CH$_3$), 4.4 1 (2H, q, —CH$_2$—), 8.61 (1H, d, C$_8$—H), J$_{H\text{-}F}$≃10.5 Hz), 9.58 (1H, s, C$_5$—H).

IR (nujol) 1,725 cm$^{-1}$, 1,705 cm$^{-1}$, 1,670 cm$^{-1}$.

9-fluoro-10-[N-(4'-ethoxycarbonyl)piperazinyl]-7-oxo-2,3-dihydro-7H-pyrido[1,2,3de][1,4]benzothiazine-6-carboxylic acid An amount of 0.45 g of the compound obtained as described above is suspended in 100 ml of dimethylformamide. At a temperature of 0°–5° C., 1.68 g of phosphorus tribromide are added, the dissolving of the product being achieved. The reaction is allowed to proceed for 10', 60 ml of water are added, and the reaction mixture is kept stirred for 1 hour. The precipitate is collected by filtration and dried (0.21 g). The filtrate is evaporated to dryness and the residue is washed with water and dried.

An amount of 0.16 g of the compound (I) with R=H;

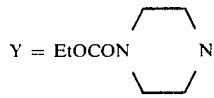

and n=0 is obtained, which is combined with the amount of 0.21 g previously obtained. Yield 86%.

| Elemental analysis | | | |
|---|---|---|---|
| Theoretical % | C = 54.15 | H = 4.78 | N = 9.97 |
| Found % | C = 54.24 | H = 4.76 | N = 9.91 |

$^1$H-NMR (CF$_3$COOH—TMS) δppm 1.42 (3H, t, CH$_3$), 3.5 (6H, m), 3.93 (4H, m), 4.4 (2H, q, CH$_2$), 5.08 (2H, m, —S—CH$_2$—), 8.13 (1H, d, C$_8$—$\underline{H}$, J$_{H-F}$≃10.7 Hz), 9.32 (1H, s, C$_5^*$—$\underline{H}$)

IR (nujol) 1,680 cm$^{-1}$, 1,708 cm$^{-1}$. m.p. 313°–315° C.

9-Fluoro-10-(N-piperazinyl)-7-oxo-2,3-dihydro-7H-pyrido[1,2,3 de][1,4]benzothiazine-6-carboxylic acid An amount of 0.87 g of the compound (I) with R=H;

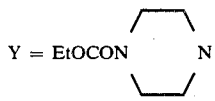

and n=0, obtained as described above, is suspended in 45 ml of sodium hydroxide at 5% concentration. The mixture is refluxed and after 30' the product is completely dissolved. The reaction mixture is cooled and treated with 2N hydrochloric acid up to pH 2. The precipitate is washed with EtOH.

After drying, 0.71 g of the compound (I) with R=H,

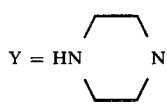

and n=0, hydrochloride are obtained. Yield 89%.
M.p. 335°–336° C.

$^1$H-NMR (CF$_3$COOH—TMS) δppm 3.75 (10H, m), 5.18 (2H, m, S—CH$_2$), 8.20 (1H, d, C$_8$—$\underline{H}$, J$_{H-F}$≃11 Hz), 9.42 (1H, s, C$_5$—$\underline{H}$)

| Elemental analysis | | | |
|---|---|---|---|
| Theoretical % | C = 49.80 | N = 4.44 | H = 10.88 |
| Found % | C = 49.93 | N = 4.24 | H = 10.53 |

EXAMPLE 7

Preparation of the compound of general formula (I) wherein R=H;

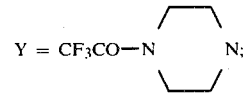

and n=0

9-Fluoro-10[N(4'-trifluoroacetyl)-piperazinyl]7-oxo-2,3-dihydro-7H-pyrido[1,2,3de][1,4]benzothiazine-6-carboxylic acid An amount of 0.2 g of the compound (I) with R=H;

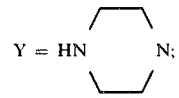

and n=0, prepared as in the preceding Example, and 7.55 g of trifluoroacetic anhydride are introduced in 3 ml of acetic acid within a reaction vessel provided with condensing cooler and calcium chloride vent. The reaction mass is heated at about 80° C. over 2 hours, is cooled, evaporated, and the residue is collected with water. The insoluble solid is filtered off and dried. An amount of 0.2 g of product is obtained with a yield of 79% having the following characteristics:

M.p. 308°–312° C.

| Elemental analysis: | | | |
|---|---|---|---|
| Theoretical % | C = 48.55 | H = 3.39 | N = 9.43 |
| Found % | C = 48.14 | H = 3.60 | N = 9.12 |

IR (nujol) 1,712 cm$^{-1}$, 1,675 cm$^{-1}$, 1,611 cm$^{-1}$.

$^1$H-NMR (CF$_3$COOH—TMS) δppm 3.6 (6H, m), 4.08 (4H, m), 5.12 (2H, m, S—CH$_2$), 8.18 (1H, d, C$_8$—$\underline{H}$, J$_{H-F}$≃10.5 Hz), 9.35 (1H, s, C$_5$—$\underline{H}$).

EXAMPLE 8

Preparation of the compound of general formula (I) wherein R=H;

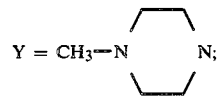

and with n equal to 1 and to 0 respectively

9-Fluoro-10[N-(4'-methyl)piperazinyl]-7-oxo-2,3-dihydro-7H-pyrido-[1,2,3de][1,4]benzothiazine-1-oxido-6-carboxylic acid An amount of 0.8 g of the sulphoxide:

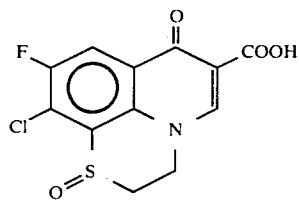

is suspended in 150 ml of toluene with 2.5 g of N-methyl piperazine. The reaction mass is refluxed for 10 hours and filtered while being still warm. The precipitate collected on the filter is constituted by about 100 mg of the starting product.

From the filtrate, the product of nucleophilic substitution precipitates on cooling, and is collected by filtration (a). By evaporating the toluene a second precipitate (b) is recovered, which, after washing with ethanol and drying, is combined with the preceding one.

A total amount of 0.4 g of 9-fluoro-10-[N-(4'-methyl)-piperazinyl]-7-oxo-2,3-dihydro-7H-pyrido[1,2,-3de][1,4]-benzothiazine-1-oxido-6-carboxylic acid hydrochloride [compound (I) with R=H;

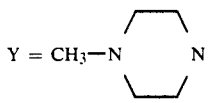

and n=1] is obtained.
Yield 43%.

9-Fluoro-10[N-(4'-methyl)-piperazinyl]-7-oxo-2,3-dihydro-7H-pyrido[1,2,3de][1,4]benzothiazine-6-carboxylic acid An amount of 0.3 g of the compound (I) with R=H;

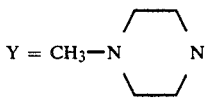

and n=1, obtained as described above, is dissolved in 40 ml of dimethylformamide and to it 0.97 g (0.35 ml) of phosphorus tribromide are added at 0°–5° C. The reaction is allowed to proceed at low temperature for 20'. To the reaction mass 30 ml of water are added. The reaction mass is evaporated, and the solid is washed with a small amount of water and then with ethanol. An amount of 0.19 g of 9-fluoro-10[N-(4'-methyl)-piperazinyl]-7-oxo-2,3-dihydro-7H-pyrido[1,2,3de][1,4-]benzothiazine-6-carboxylic acid hydrobromide [compound (I) with R=H;

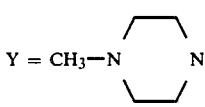

and n=0] is obtained.
Yield 59%.
m.p. 322°–324° C.

| Elemental analysis: | | | |
|---|---|---|---|
| Theoretical % | C = 45.96 | H = 4.31 | N = 9.45 |
| Found % | C = 45.78 | H = 4.24 | N = 9.46 |

$^1$H-NMR (CF$_3$COOH—TMS) ppm 3.2 (3H, N—CH$_3$), 3.8 (10H, m), 5.15 (2H, m, CH$_2$—S), 8.18 (1H, d, C$_8$—H, J$_{H-F}$=10.5 Hz), 9.4 (1H, s, C$_5$—H).

EXAMPLE 9

Preparation of the compound of general formula (I) wherein R=CH$_3$; Y=Cl and n=0

An amount of 2 g of disulphide (XIII) (obtained from 6-fluoro-7-chloro-2-amino-benzothiazole, by treatment with NaOH as described in Example 1) is introduced in 15 ml of EtOH and treated with 0.75 g of KOH in ethanol and then 1.9 ml of monochloroacetone are slowly added thereto.

The reaction is allowed to proceed for 1 hour under refluxing conditions. The reaction mass is evaporated and the residue is extracted with chloroform.

The combined chloroform phases are washed with water and thoroughly dried. The residue obtained by evaporation is reduced with an excess of NaBH$_4$ in ethanol at 50° C. over 1 hour. The ethanol is evaporated and the residue is diluted with chloroform.

After percolation on a silica gel column and evaporation of the eluted phase, 0.94 g of 7-fluoro-8-chloro-3,4-dihydro-3-methyl-2H-1,4-benzothiazine [compound (II) with Y=Cl and R=CH$_3$] are obtained (Yield 38.7%).

| Elemental analysis: | | | |
|---|---|---|---|
| Theoretical | C = 49.67% | H = 4.17% | N = 6.43% |
| Found | C = 49.87% | H = 4.14% | N = 6.48% |

An amount of 1.47 g of the compound (II) with Y=Cl and R=CH$_3$, obtained as described above, is reacted with 1.85 ml of ethyl ethoxymethylenemalonate at 120° C. under stirring over 1 hour and 45'. An amount of 5.4 g of polyphosphoric acid is then added, and the temperature is raised to 160° C. for one hour. The reaction mass is cooled and treated with icy water. An oil separates, which is broken up by stirring.

The solid formed is collected by filtration and washed with water and without any further purification is introduced in 10 ml of NaOH at 10% concentration, and refluxed for 1 hour. The sodium salt which is formed is poorly soluble under the reaction conditions and precipitates. The reaction mass is cooled, is poured into icy water and is made acid with HCl at 10% concentration. The product obtained is filtered off and washed with water.

An amount of 1.45 g (yield 68%) of 9-fluoro-10-chloro-3-methyl-7-oxo-2,3-dihydro-7H-pyrido[1,2,-3de][1,4]benzothiazine-6-carboxylic acid [compound (I) with R=CH$_3$ and Y=Cl and n=0] is obtained.

| Elemental analysis: | | | |
|---|---|---|---|
| Theoretical % | C = 49.77 | H = 2.89 | N = 4.46 |
| Found % | C = 49.81 | H = 2.91 | N = 4.49 |

EXAMPLE 10

Preparation of the compound of general formula (I) wherein R=CH₃,

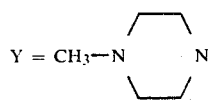

and n=0

An amount of 1.5 g of compound (IV) (Y=Cl and R=CH₃) is suspended in acetic acid as 75% concentration. To it 30 mg of KBr are added and, while following the reaction with a potentiometer equipped with Pt-calomel electrodes, a 0.065M solution of lead tetraacetate in acetic acid is slowly added at the temperature of 30° C. The potential varies from a value of 480 mV to a value exceeding 1,000 mV after the addition of about 90 ml of lead tetraacetate. The solvent is thoroughly evaporated and the sulphoxide is crystallized from acetic acid.

An amount of 1.39 g (yield 88.2%) is obtained of 9-fluoro-10-chloro-3-methyl-7-oxo-2,3-dihydro-7H-pyrido[1,2,3 de][1,4]benzothiazine-1-oxido-6-carboxylic acid [compound (V) with R=CH₃ and Y=Cl] having the following elemental analysis:

| | | | |
|---|---|---|---|
| Theoretical | C = 47.35% | H = 2.75% | N = 4.25% |
| Found | C = 47.41% | H = 2.69% | N = 4.36% |

IR (nujol)=1,048 cm⁻¹, 1,030 cm⁻¹.

An amount of 0.75 g of sulphoxide (V) is suspended in 140 ml of toluene with 2.5 ml of N-methylpiperazine. The reaction mass is refluxed for 10 hours and is then filtered, while being still warm.

The precipitate remaining on the filter is constituted by the starting product.

From the filtrate precipitates on cooling the product of nucleophilic substitution, which is recovered by filtration. On evaporation, additional precipitate is formed which, after washing with ethanol and drying, is combined with the preceeding one.

An overall amount of 0.46 g of 9-fluoro-10[N-(N′-methyl)piperazinyl]-3-methyl-7-oxo-2,3-dihydro-7H-pyrido[1,2,3de][1,4]benzothiazine-1-oxido-6-carboxylic acid hydrochloride [compound (VI) with R¹=CH₃] is obtained (yield 47%).

An amount of 0.4 g of sulphoxide hydrochloride (VI) is dissolved in dimethylformamide and to it 0.97 g (0.35 ml) of phosphorus tribromide are added at 0°–50° C. The reaction is allowed to proceed at low temperature over 20 minutes. To the reaction mass 20 ml of water are added. The reaction mass is evaporated and the solid residue is washed with a small amount of water and then with ethanol. An amount of 0.29 g of 9-fluoro-10-[N-(N′-methyl)-piperazinyl]-3-methyl-7-oxo-2,3-dihydro-7H-pyrido[1,2,3de][1,4]benzothiazine-6-carboxylic acid hydrobromide [compound (I) with R=CH₃;

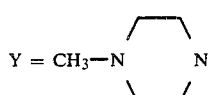

and n=0] is obtained (Yield 70%).

| | | | |
|---|---|---|---|
| Theoretical | C = 47.17% | H = 4.40% | N = 9.17% |
| Found | C = 47.24% | H = 4.53% | N = 9.25% |

EXAMPLE 11

Preparation of the compound of general formula (I) wherein R=CH₃, Y=F and n=0

An amount of 4 g of 2,3,4-trifluoro-nitrobenzene (obtained according to J.A.C.S. 81, 94, 1959) is heated in 50 ml of Me₂SO at 90° C. with 6.8 g of sodium sulphide for 2 hours. The reaction mass is cooled, the insoluble residue is filtered off and the filtrate is evaporated. The raw solid obtained (6.89 g) is treated in 30 ml of acetic acid with 20 g of iron dust. The mixture is heated in a water bath, initially cautiously, then under refluxing conditions for 1 hour. The reaction mass is filtered while being still warm, and the precipitate is washed with acetic acid. The filtrate is treated at high temperature with 5 ml of hydrochloric acid at 37% concentration, and is kept at 80° C. for 1 hour. The mass is diluted with water and made neutral with sodium hydroxide. The solution is extracted with chloroform. The combined chloroform phases are dried and evaporated. The residue (1.37 g) is introduced in 15 ml of ethanol, to the mixture 6.75 g of KOH and 1.9 ml of monochloro-acetone are added. The mixture is refluxed for 1 hour. The reaction mass is evaporated and the residue is extracted with chloroform. The combined chloroform phases are dried on sodium sulphate and evaporated. The residue from the evaporation is reduced with an excess of sodium borohydride in ethanol at 50° C. for 2 hours. The ethanol is evaporated, the residue is diluted with chloroform and is percolated on a silica gel column. After the evaporation of eluted chloroform, 0.83 g of 7.8-difluoro-3,4-dihydro-3-methyl-2H-1,4-benzothiazine [compound (II) with Y=F and R=CH₃] are obtained.

| | | | |
|---|---|---|---|
| Theoretical | C = 53.72% | H = 4.51% | N = 6.96% |
| Found | C = 53.02% | H = 4.83% | N = 6.78% |

An amount of 0.83 g of compound (II) with Y=F and R=CH₃, obtained as described above, is treated under the same conditions, and by the same way as described in Example 9. An amount of 0.95 (yield 77%) of 9,10-difluoro-3-methyl-7-oxo-2,3-dihydro-7H-pyrido[1,2,-3de][1,4]benzothiazine-6-carboxylic acid [compound (I) with R=CH₃; Y=F and n=0] is obtained.

| | | | |
|---|---|---|---|
| Theoretical % | C = 52.52 | H = 3.05 | N = 4.71 |
| Found % | C = 52.86 | H = 3.13 | N = 4.84 |

EXAMPLE 12

Preparation of the compound (I) with R=CH₃;

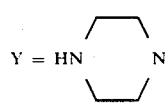

and n=0

By means of a process similar to that described in Example 10, 0.9 g of compound (IV) (Y=F and R=CH₃) are oxidized to the sulphoxide with a yield of 86%.

An amount of 0.82 g of the sulphoxide obtained is suspended in 25 ml of dimethyl sulphoxide and to the suspension 1.85 g of N-ethoxycarbonylpiperazine are added. The mixture is heated at 140° C. over one hour. After that the reactants have been dissolved, a precipitate is formed which is recovered by filtration. The filtrate is evaporated and the residue is treated with ethanol and dimethyl ether. An additional precipitate is obtained, which is combined with the preceding one. A total amount of 0.9 g (yield 76%) of compound (VI) with $R^1=CH_3CH_2OCO$ is obtained.

| Elemental analysis: | | | |
|---|---|---|---|
| Theoretical % | C = 53.20 | H = 4.91 | N = 9.30 |
| Found % | C = 53.31 | H = 4.87 | N = 9.23 |

An amount of 0.85 g of compound (VI) ($R^2=CH_3CH_2OCO$) is suspended in 50 ml of dimethylformamide and 3 g of phosphorus tribromide are added to the suspension at 0°-5° C. The suspended matter is immediately dissolved. After 10 minutes of reaction, to the reaction mass 80 ml of water are added. After one hour of stirring, the precipitate is collected by filtration and is immediately transferred in to 40 ml of sodium hydroxide at 5% concentration. The mixture is refluxed and after 30 minutes the product has been completely dissolved. After cooling, the reaction mass is treated with 2N hydrochloric acid up to pH 2. The precipitate is collected and washed with ethanol. After the complete evaporation, 0.559 g (yield 74.3%) of the compound (I) with R=CH₃;

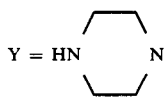

and n=0, as hydrochloride, are obtained.
M.p. 339°-344° C.

| Elemental analysis | | | |
|---|---|---|---|
| Theoretical % | C = 51.06 | H = 4.54 | N = 10.51 |
| Found % | C = 51.31 | H = 4.60 | N = 10.59 |

EXAMPLE 13

Preparation of the compound (I) with R=H; Y=Cl; n=0

The compound 3-chloro-4-fluoroaniline (XI) is reacted with KSCN and bromine in acetic acid, as described in example 1; a mixture of 2-amino-6-fluoro-7-chloro benzothiazine (XII) and of its isomer with chorine in the 5-position (50:50 ratio) is obtained with an overall yield of 87%.

21 grams of this mixture are treated with 50% NaOH under reflux conditions up to complete elimination of ammonia. After cooling the reaction mixture is filtered through active coal and the obtained solution is acidified with acetic acid.

A precipitate forms which is filtered, washed with water, dried and extracted with boiling ethanol. The ethanolic solution is concentrated up to 130 ml and added with 6.8 g of NaOH dissolved into 40 ml of water and with 17.5 ml of 1-bromo-2-chloro-ethane.

The mixture is kept boiling over 4 hours, cooled, added with water and extracted with chloroform.

The chloroform phase is dried on sodium sulphate and evaporated so obtaining the compound (II) wherein R=H and Y=Cl with a yield of 80%. The two isomers are then separated by treatment with oxalyc acid and fractional crystallization of the formed oxalates.

The ¹H-NMR of the compound (II) wherein R=H and Y=Cl is quite identical to the one of the same compound (II) obtained according to example 1.

An equally efficient separation of the isomers has been obtained by flash-cromatography.

158 grams of the thus prepared pure compound (II) is reacted with 1.9 ml of ethyl ethoxymethylenemalonate at 120° C. under stirring for about 2 hours; 5.5 g of polyphosphoric acid are then added, keeping the temperature at 160° C. for about one hour.

At the end of this time, the reaction mass is cooled and treated with icy water. The obtained dense oil is stirred and the formed solid filtered off and wahed with water.

2.35 g of compound (III) with R=H and Y=Cl are obtained with a yield of 92%.

Also for compound (III), the ¹H-NMR is quite corresponding to that given in example 1.

One gram compound (III) is refluxed with 45 ml of 10% NaOH for 1 hour. The mixture is cooled, poured into icy water and then made acid with HCl, filtered and washed with water.

The compound (I) with R=H, Y=Cl and n=0 is obtained with a yield as high as 90%.

EXAMPLE 14

Preparation of the compound (I) with R=H;

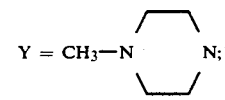

n=0

3 grams of compound (I) of example 13 are suspended in a solution constituted by 300 ml of H₂O and 1,000 ml of acetic acid and 70 mg of KBr are added. Then 200 ml of a 0.065M solution of Pb(OAc)₄ in acetic acid are slowly added at the temperature of 40° C.

When the addition of Pb(OAc)₄ is ended, the solvent is evaporated and the product (V) where R=H and Y=Cl is obtained with a yield of 85%. 16 cc of methylpiperazine are added to 6.5 g of above compound (V) suspended into 100 cc of DMF; the temperature is raised to 100°-105° C. in order to obtain a clear solution which is than kept under stirring over 45 minutes, at 90°–95° C.

The solvent is evaporated and the residue, taken up with ethanol, gives with 75% yield the sulphoxide 9-fluoro-10-[N-(4'-methyl)piperazinyl]-7-oxo-2,3-dihydro-7H-pyrido[1,2,3de][1,4]benzothiazine-1-oxido-6-carboxylic acid (compound I where R=H;

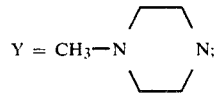

n=1)

$^1$H-NMR (CF$_3$COOH—TMS) δppm 3.3 (3H, d, N—CH$_3$) 3.9 (10H, m, N—CH$_2$) 5.4 (2H, m, S—CH$_2$) 8.77 (1H, d, C$_8$—H, J$_{H\text{-}F}$~10.5 Hz) 9.68 (1H, s, C$_5$—H)

| Elemental analysis | C | H | N |
|---|---|---|---|
| Theoretical % | 53.82 | 4.78 | 11.07 |
| Found % | 53.34 | 4.65 | 10.82 |

The above identified sulphoxide is dissolved into DMF (5 g in 250 cc), the solution is cooled at 0°–5° C. with ice-salt and 4 cc of PCl$_3$ are dropped therein. The mixture is allowed to react over 15 minutes, 150 cc of water are added and the whole is kept under stirring at room temperature for about 1 hour.

The solvent is evaporated, the residue is taken up with ethanol and filtered.

The 9-fluoro-10[N-(4'-methyl)piperazinyl]-7-oxo-2,3-dihydro-7H-pyrido[1,2,3de][1,4]-benzothiazine-6-carboxylic acid hydrochloride is obtained with a yield of 93%.

It may be further crystallized from a warm mixture ethanol/water in a ratio 7/3. Melting point 315°–320° C.

$^1$H-NMR (CF$_3$COOH—TMS) δppm 3.2 (3H, d, N—CH$_3$) 3.8 (10H, m, N—CH$_2$) 5.15 (2H, m, CH$_2$—5) 8.18 (1H, d, C$_8$—H J$_{HF}$~10.5 Hz) 9.4 (1H, s, C$_5$—H) UV (H$_2$O) λ$_{max}$=245 mμ and 296 mμ.

We claim:

1. A process for the preparation of a pyrido-benzothiazine compound of the formula:

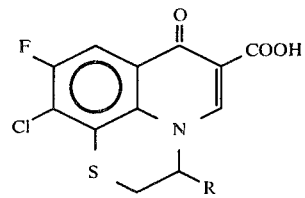

wherein R is H or CH$_3$, which comprises:
(a) reacting 3-chloro-4-fluoroaniline with potassium thiocyanate and bromine to produce 2-amino-6-fluoro-7-chlorobenzothiazole,
(b) reacting 2-amino-6-fluoro-7-chlorobenzothiazole with sodium hydroxide to produce the disulfide of 2-amino-5-fluoro 6-chlorothiophenol,
(c) reacting said disulfide with sodium monochloroacetate to produce 7-fluoro-8-chloro-2H-1,4-benzothiazin-3(4H)-one,
(d) reducing 7-fluoro-8-chloro-2H-1,4-benzothiazin-3(4H)-one to produce 7-fluoro-8-chloro-3,4-dihydro-2H-1,4-benzothiazine,
(e) reacting 7-fluoro-8-chloro-3,4-dihydro-2-H-1,4-benzothiazone with ethyl ethoxymethylenemalonate and cyclyzing the intermediate formed with polyphosphoric acid to produce ethyl 9-fluoro-10-chloro-7-oxo-2,3-dihydro-7H-pyrido[1,2,3de][1,4-]benzothiazine-6-carboxylate, and
(f) hydrolyzing said ethyl carboxylate to produce the corresponding carboxylic acid.

2. A process according to claim 1, wherein the 7-fluoro-8-chloro-2H-1,4-benzothiazine-3(4H)-one is reduced with sodium borohydride.

3. A process according to claim 1, wherein the 7-fluoro-8-chloro-2H-1,4-benzothiazine-3(H)-one is reduced with lithium aluminum hydride.

4. A process according to claim 1, wherein the reaction of the benzothiazone in step (e) with ethyl ethoxymethylenemalonate is carried out at a temperature from 80° to 160° C.

5. A process according to claim 1, comprising the additional step of oxidizing the carboxylic acid of step (f) with lead tetraacetate to produce the corresponding sulphoxide.

* * * * *

UNITED STATES PATENT AND TRADEMARK OFFICE
CERTIFICATE OF CORRECTION

PATENT NO.    :  4,668,784
DATED         :  May 26, 1987
INVENTOR(S)   :  Giuseppe MASCELLANI et al It is certified that error appears in the above-identified patent and that said Letters Patent is hereby corrected as shown below:

Columns 7-8 and 9-10, under "TABLE 1" in the heading of the table after "Activity expressed as MIC (mcg/ml) for compounds of formula" change the structural formula to read:

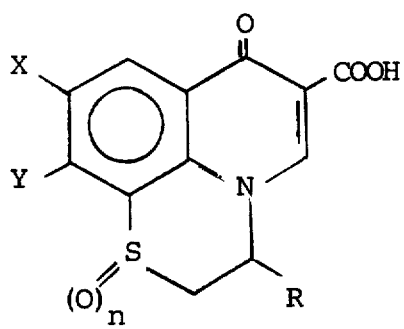

Signed and Sealed this

Twenty-ninth Day of May, 1990

Attest:

HARRY F. MANBECK, JR.

Attesting Officer

Commissioner of Patents and Trademarks